United States Patent

Rahimzadeh

[11] Patent Number: 5,288,148
[45] Date of Patent: Feb. 22, 1994

[54] DETERMINING THE TEMPERATURE AT WHICH A SUBSTANCE CHANGES STATE

[76] Inventor: Bizhan Rahimzadeh, 101a Blackburn Street, Radcliffe, Manchester, M26 9WQ, England

[21] Appl. No.: 773,619
[22] PCT Filed: May 16, 1990
[86] PCT No.: PCT/GB90/00751
§ 371 Date: Nov. 15, 1991
§ 102(e) Date: Nov. 15, 1991
[87] PCT Pub. No.: WO90/14592
PCT Pub. Date: Nov. 29, 1990

[30] Foreign Application Priority Data

May 16, 1989 [EP] European Pat. Off. ............ 89304936

[51] Int. Cl.$^5$ ............................................. G01N 25/04
[52] U.S. Cl. ......................................... 374/19; 374/20
[58] Field of Search ...................... 374/17, 18, 19, 20

[56] References Cited

U.S. PATENT DOCUMENTS 3,926,052 12/1975 Bechtel ................................. 374/20
4,908,835 3/1990 Nishiuchi et al. .................... 374/20

FOREIGN PATENT DOCUMENTS 1165544 10/1958 France ................................. 374/20
1188692 10/1985 U.S.S.R. ............................. 374/20

Primary Examiner—William A. Cuchlinski, Jr.
Assistant Examiner—Diego F. F. Gutierrez

[57] ABSTRACT

Infra-red light from an emitter is directed through a glass slide to an area on which a solid substance is located. Light reflected from the undersurface of the solid substance is received by a receiver. The substance is heated by a strip heater. When the substance changes state, the amount of reflected light arriving at the receiver varies, and information coming from an electronic thermometer records the temperature at which the change of state has occurred.

16 Claims, 1 Drawing Sheet

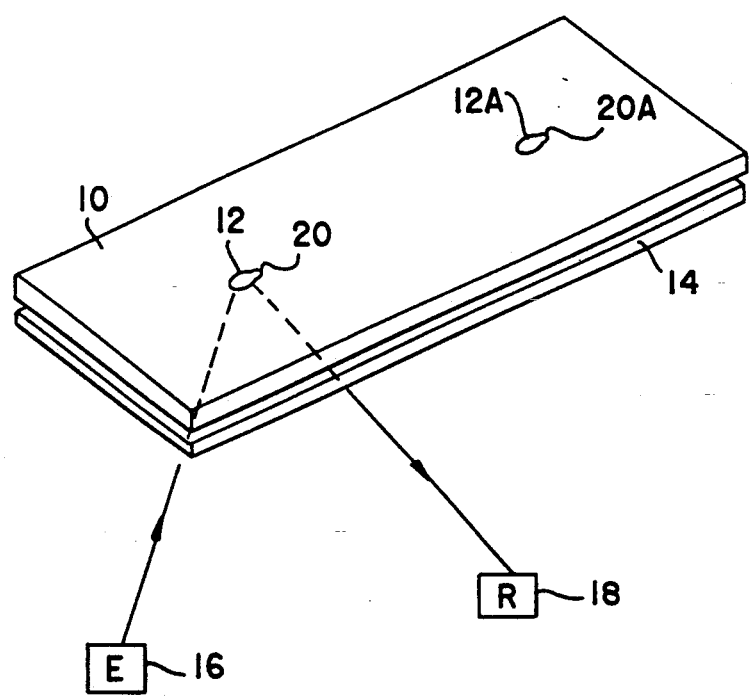

DETERMINING THE TEMPERATURE AT WHICH A SUBSTANCE CHANGES STATE

BACKGROUND OF THE INVENTION

1. Field of the Invention

The present invention relates to a method of and apparatus for determining the temperature at which a substance changes state and is particularly, although not exclusively, concerned with determining the melting point of a substance.

2. DESCRIPTION OF THE RELATED ART

A prior method of determining the melting point of a substance comprises emitting light from a source and directing that light at a solid substance. A photocell is located on the other side of the substance to receive any light transmitted through the substance. The substance is then heated. Some melted substances allow more light to be transmitted therethrough when they are melted and the increase in light transmitted through the substance indicates the melting point temperature of the substance. However, some substances become frothy or are dark when they melt and thus there may be no light, or no change in light received by the photocell, or no such discernible change when the substance melts thereby rendering determination of the melting point impossible with this method. Furthermore, the substance is placed in a capillary tube prior to having light directed at it which is a difficult and messy operation to perform.

An alternative prior method of determining the melting point of a substance is shown in GB 2 202 941A (Fisons) in which light is emitted downwardly on to a solid sample which is being heated. When the sample becomes molten, light is no longer scattered by the sample but is instead reflected upwardly, and the change determined by the detector is used to indicate that the sample has melted. However, as the temperature of the heating block is continually rising, and as there is a delay between the time when the bottom of the sample melts and the time when the top surface melts, by the time the change in reflection is determined the temperature of the heating block will have risen slightly and the recorded melting temperature will not be the actual melting temperature. Furthermore, the location of the light source and light detector above the sample plate causes the source and detector to be in the way when the plate is loaded and unloaded, and the source and detector are exposed to the environment and any splashes or vapour rising from the sample thereby becoming dirty and impairing their function.

SUMMARY OF THE INVENTION

It is an object of the present invention to attempt to overcome at least some of the above disadvantages.

According to one aspect of the present invention a method of determining the temperature at which a substance changes state comprises monitoring a change in light reflected from the substance when the substance undergoes at least a partial change in state is characterised in that the light reflected from a downwardly facing surface is monitored. The method may enable the temperature at which the substance changes state to be determined as soon as the substance starts to change state as the substance melts first at the downwardly facing surface thereof and that is where reflected light is monitored from. Furthermore, monitoring is done from beneath the substance allowing the substance to be monitored from above without independence from the monitoring region and permitting the monitoring to be unaffected from any vapours rising from the substance. Such a method may provide an accurate means for determining the temperature at which the substance changes state, even when there may be no change in the light (if any) which can be transmitted through the substance in the different states, as it has been found that there is a change in reflectivity for all tested substances when there is a change in state.

BRIEF DESCRIPTION OF THE DRAWING

The single Figure is a perspective view of a sample being tested according to this invention.

DESCRIPTION OF PREFERRED EMBODIMENTS

The method may comprise loading a substance to be monitored into a position to be monitored from above the region where the monitoring of the reflected light is done.

The method may comprise monitoring light reflected through a supporting surface for the substance.

The method may comprise monitoring reflected visible or invisible light such as infra red light.

The method may comprise heating the substance for instance by a strip heater.

The method may comprise monitoring at least a partial change of state from a solid to a liquid in which case the light may be transmitted through or absorbed by the liquid, either totally or partially. The method may comprise determining the melting point of the substance.

The method may comprise determining the temperature at which a crystalline powder changes state.

The method may further include monitoring the temperature of an area spaced from the substance and, alternatively or additionally, monitoring the temperature of the substance, and that area may include the same substance.

The method may comprise mounting a smear of substance.

The method may comprise directing light towards the substance.

The method may comprise cooling the substance, or cooling a surface on which it is mounted, after it has changed state possibly by cooling with a fan.

According to another aspect of the present invention, monitoring apparatus including a receiver arranged to receive light reflected from a substance located at a test region, temperature monitoring means and monitoring means arranged to determine when there has been a change in light reflected from a substance located in the test region occasioned by such a substance at least partially changing state, is characterised in that the receiver is arranged to receive light through a supporting surface for a substance located at the test region and from a downwardly facing surface of a substance located at the test region.

The apparatus may include a light source, which may comprise visible, invisible or infra red light, arranged to direct light at a substance located in the test region.

The apparatus may include heating means arranged to heat a substance located in the test region. The heater may comprise a strip heater. The heater may include an opening located beneath the test region.

The apparatus may include temperature monitoring means arranged to monitor the temperature of a substance located in the test region. The temperature monitoring means may, alternatively or additional, be arranged to monitor the temperature of a region spaced from the test region and may be arranged to monitor the temperature on a surface comparable to a surface arranged to provide support for a substance to be monitored at the test region.

The apparatus may include means arranged to store or indicate the temperature at which a substance has at least partially changed state.

The present invention also includes a monitoring apparatus when used in a method as herein described.

The present invention may be carried into practice in various ways, but one embodiment will now be described by way of example and with reference to the accompanying drawing which is a schematic representation of melting point determination apparatus.

A glass slide 10 has two areas 12 and 12A on each of which smear of the sample to be tested is located. The slide 10 is placed on a strip heater 14 and light from an emitter 16 is directed through an opening in the strip heater, through the glass slide, against the downwardly facing surface of the smear of sample in area 12. Any light reflected from the downwardly facing surface of the smear is directed towards a receiver 18.

To conduct a test to determine the melting point of a substance, infra red light from the emitter 16 is directed towards the solid smear on the slide, and heat is supplied gradually to the substance by the heater 14. The temperature of the substance in area 12 is monitored by an electronic thermometer 20 and the temperature in area 12A is monitored by a further electronic thermometer 20A.

While the substance in area 12 remains solid, the majority of the infra red light is reflected from the sample back to the receiver 18. As soon as the substance turns to liquid either the light from the emitter will mostly pass upwardly through the sample (should the liquid be relatively clear) or most of the light will be absorbed into the liquid (should the liquid be dark or frothy). In any event there will be a change in the amount of light arriving at the receiver when the substance melts.

The temperature of the thermometer 20 is monitored and recorded at the instant when there is a change in the reflected light.

The purpose of the thermometer 20A is to confirm that the temperature of the sample smear being tested is accurate. The temperature from the thermometer 20A is also monitored and recorded and compared to the temperature from the thermometer 20. Bearing in mind that the conditions for both areas 12 and 12A are the same, the temperatures of those areas should also be the same. If they are not the same then the test is repeated. In an alternative embodiment there is only a thermometer at the area 12A, away from the sample being tested, and the temperature of that thermometer is monitored.

The apparatus is particularly suited to determining the melting point of crystalline powders. Should noxious gasses be emitted on melting then the extremely small size of smear which is tested limits the amount of gas which is emitted. Furthermore, the heater may be arranged to be switched off automatically when the substance melts. Alternatively or additionally a fan may cool the substance once melted or alternatively or additionally the apparatus may be encased in an air tight unit.

In an alternative embodiment, the slide 10 remains in the illustrated position and the product to be tested is placed on top of the glass over the test area. The thermometer 20 is located on top of the slide in the area 12A to measure the temperature on the top surface of the slide and therefore measure what must be the temperature on the undersurface of the sample. When the test is finished the slide remains in position and is wiped clean to be ready for the next sample.

As the monitoring of reflectivity is done from beneath the sample, the emitter 16 and receiver 18 can be encased to be protected from pollution from the environment, and they will not be contaminated by liquid or vapour emanating from the sample. Furthermore, the slide 10 can be loaded from above, without the emitter or receiver getting in the way.

Where a change in the reflected light is being monitored this includes a situation where no light is initially reflected or where no light is subsequently reflected following at least a partial change in state.

I claim:

1. A method of determining the temperature at which a substance changes state comprising impinging a light beam on a region of the back side surface of a substance, directly heating said back side of said substance to at least its melting point with means which does not interfere with said impinging light beam or a reflection thereof from said back side surface, monitoring a change in light reflected from the back side surface of the substance when the substance undergoes at least a partial change in state as a function of the temperature of said surface, and measuring the temperature at which the substance changes state, said change of state being indicated by said change in light reflectance.

2. A method as claimed in claim 1 further comprising loading the substance into a position to be monitored from above the region where the monitoring of the reflected light is done.

3. A method as claimed in claim 1 wherein said monitoring is of light reflected through a supporting surface for the substance.

4. A method as claimed in claim 1 wherein said reflected light is infra red light.

5. A method as claimed in claim 1 wherein said change of state is from a solid to a liquid.

6. A method as claimed in claim 1 further comprising monitoring the temperature of an area spaced from the substance.

7. A method as claimed in claim 1 wherein said reflected light is visible light.

8. A method as claimed in claim 1 wherein said reflected light is invisible light.

9. A method as claimed in claim 1 in which the substance being monitored comprises a crystalline powder and the method comprises monitoring when said crystalline powder changes state.

10. A method as claimed in claim 1 further comprising cooling the substance after it has changed state.

11. A method as claimed in claim 1 wherein said temperature at which said substance changes state is the temperature at which the substance melts.

12. Monitoring apparatus for determining the temperature at which the surface of a substance changes state comprising:

a substance, whose state is to be determined, disposed in a test region in a position such that a back side surface thereof is substantially downwardly directed;

means for emitting light spaced from said substance and located and positioned to impinge light emitted therefrom against said downwardly directed back side surface of said substance, said light being reflected therefrom;

means for directly heating at least a region of said downwardly directed back side surface of said substance to at least a temperature at which said region changes state, which heating means does not interfere with light emitted or reflected thereof;

means for measuring the temperature at which said back side surface of said substance changes state; and means, disposed below said downwardly directed back side surface, for determining a change in said reflected light indicative of said change of state.

13. Apparatus as claimed in claim 12 in which said heating means includes an opening located beneath the test region.

14. Apparatus as claimed in claim 12 further including temperature monitoring means arranged to monitor the temperature of a region spaced from the test region.

15. Apparatus as claimed in claim 12 further including temperature monitoring means spaced from the test area arranged to monitor the temperature on a surface comparable to a surface arranged to provide support for the substance to be monitored at the test region.

16. Monitoring apparatus as claimed in claim 12 further including means supporting said downwardly directed back side surface of said substance which is at least partially transparent to said impinged and reflected light.

* * * * *